(12) United States Patent
Sakanaka et al.

(10) Patent No.: US 6,579,853 B2
(45) Date of Patent: Jun. 17, 2003

(54) BRAIN CELL OR NERVE CELL-PROTECTIVE AGENTS COMPRISING GINSENOSIDE RB₁

(75) Inventors: Masahiro Sakanaka, Ehime-ken (JP); Junya Tanaka, Ehime-ken (JP); Kohji Sato, Hamamatsu (JP)

(73) Assignee: Japan Science and Technology Corporation, Saitama-ken (JP)

( * ) Notice: Subject to any disclaimer, the term of this patent is extended or adjusted under 35 U.S.C. 154(b) by 0 days.

(21) Appl. No.: 09/887,399

(22) Filed: Jun. 22, 2001

(65) Prior Publication Data

US 2002/0002141 A1 Jan. 3, 2002

(30) Foreign Application Priority Data

Dec. 22, 1998 (JP) .......................................... 10-365560

(51) Int. Cl.⁷ .......................... A61K 31/715; A61K 9/08
(52) U.S. Cl. .......................... 514/26; 514/53; 514/169; 514/27; 424/195.11; 536/4.1
(58) Field of Search .......................... 514/26, 53, 169, 514/27; 424/195.11; 536/4.1

(56) References Cited

U.S. PATENT DOCUMENTS 5,137,878 A * 8/1992 Pang et al. .................... 514/54
5,589,182 A * 12/1996 Tashiro et al. ............... 424/423
6,083,932 A * 7/2000 Pang et al. .................... 514/54

FOREIGN PATENT DOCUMENTS

WO       WO 90/08315       7/1990

OTHER PUBLICATIONS

Stancheva et al. "Ginsenoside Rg1 inhibits the brain cAMP phosphodiesterase activity in young and aged rats." Gen. Pharmac vol. 24, No. 6, pp. 1459–1462, 1993.*

Jin et al. "Inhibitory effects of ginsenoside Rg1 and Rb1 on rat brain microsomal Na, K—ATPase activity." Acta Pharmacologica Sinica, 11(1), pp. 10–14. Jan. 1990.*

*Acta Pharmaceutica Sinica*, 30(9):674–678 (1995).

*Acta Pharmaceutica Sinica*, 22(1):1–5 (1987).

Y. Zhang et al., *Acta Pharamaceutica Sinica*, 17(1):44–48 (1996).

*Acta Pharmaceutica Sinica*, 32(6):406–410 (1997).

T. Wen. et al., *J. Exp. Med.*, 188(4):635–649 (1998).

B. Zhang et al., *Journal of Stroke and Cerebrovascular Diseases*, 7(1):1–9 (1998).

J. Lim et al., *Neuriscience Research*, 28:191–200 (1997).

* cited by examiner

*Primary Examiner*—Samuel Barts
*Assistant Examiner*—Devesh Khare
(74) *Attorney, Agent, or Firm*—Peter F. Corless; John B. Alexander; Edwards & Angell, LLP

(57) ABSTRACT

The present invention provides preparations for efficaciously administering ginsenoside $Rb_1$ or its salt useful as cytoprotective agents. More particularly, the present invention provides pharmaceutical compositions comprising ginsenoside $Rb_1$ or its salt for inhibiting apoptosis or apoptosis-like cell death or pharmaceutical compositions comprising ginsenoside $Rb_1$ or its salt for promoting the expression of a cell death-inhibitory gene product $Bcl-x_L$. Further, the present invention provides preparations for intravenous administration comprising ginsenoside $Rb_1$ or its salt. The above pharmaceutical compositions contain ginsenoside $Rb_1$ or its salt at low extracellular concentrations in lesion, preferably at 1 ng/ml or less and still preferably at 1 to 100 fg/ml. These compositions promote the expression of the cell death-inhibitory gene product $Bcl-x_L$ and inhibit apoptosis or apoptosis-like cell death. The above preparations for intravenous administration are useful for therapy, prevention or treatment of many diseases, in particular, brain and nervous diseases.

12 Claims, 8 Drawing Sheets

BRAIN CELL OR NERVE CELL-PROTECTIVE AGENTS COMPRISING GINSENOSIDE RB₁

TECHNICAL FIELD

The present invention relates to ginsenoside $Rb_1$ or its salt useful as cell-protective (cytoprotective) agents. More particularly, the present invention pertains to pharmaceutical compositions comprising ginsenoside $Rb_1$ or its salt for inhibiting apoptosis or apoptosis-like cell death or pharmaceutical compositions comprising ginsenoside $Rb_1$ or its salt for promoting the expression of a cell death-inhibitory or antiapoptotic gene product $Bcl-x_L$. More further particularly, the present invention pertains to pharmaceutical compositions comprising ginsenoside $Rb_1$ or its salt for intravenous administration.

BACKGROUND ART

Originally, methods for treatment of cerebral apoplexy (cerebral vascular diseases) are different among cerebral infarction, cerebral embolism, cerebral hemorrhage, transient ischemic attack and subarachnoid hemorrhage, and strictly, no effective countermeasure can be taken unless a cerebral CT inspection is performed. For example, thrombolytic agents can be used only for the treatment of cerebral infarction and cerebral embolism and are regarded as a contraindication for the treatment of cerebral hemorrhage. However, cerebral apoplexy is a serious disease resulting in a permanent disorder of higher functional activities or threatening the survival of patients, if no treatment is performed for protecting nerve cells or neurons at risk in the lesion site as early as possible. Consequently the treatment should be initiated without a moment's delay. Even the period of time for the CT inspection of brain is, to put it strongly, a factor to make the possibility of recovery smaller for the patients with cerebral apoplexy. Surely, the treatment of acute cerebral apoplexy is a struggle against not only cerebral apoplectic lesion but also a time after its onset. Quite unfortunately, at present, whatever the disease type of cerebral apoplexy (cerebral infarction, cerebral hemorrhage, cerebral embolism, subarachnoidal hemorrhage and transient ischemic attack) is, it is the actual condition that few drugs showing a potent effect, if administered immediately after the onset of cerebral apoplexy, are known.

Ginsenoside $Rb_1$ is a compound having the following chemical structure:

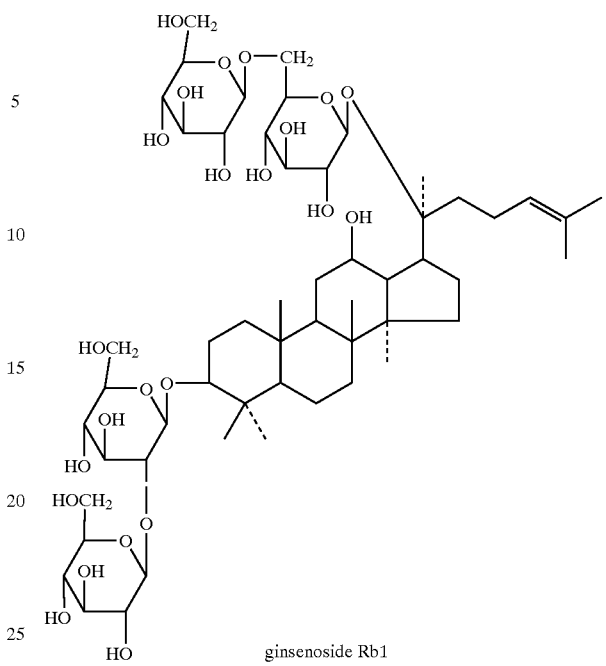

ginsenoside Rb1

Ginsenoside $Rb_1$ is a known compound with references, for example, by Shibata et al. (Shibata et al., Economic and medicinal plant research, World Scientific, Philadelphia, pp. 217–284, 1985).

Intraperitoneal administraction of ginsenoside $Rb_1$ has been reported to show a tranquilizing action on the brain (Yoshimura H. et al., Eur. J. Pharmacol., 146, 291–197, 1988), but no mechanism of the action has been elucidated. In the central nervous system, the possibility has been raised that a mixture of ginsenoside $Rb_1$ and ginsenoside $Rg_1$ (or ginsenoside $Rb_1$ or ginsenoside $Rg_1$ at the extracellular concentration from $10^{-6}M$ to $10^{-7}M$) shows some effect for Alzheimer's disease as a result of activating acetylcholine-containing nerve cells (U.S. Pat. No. 5,137,878: Composition and method for treatment of senile dementia). However, since it can not be said that the main cause of Alzheimer's disease is a functional disturbance of acetylcholine-containing nerve cells, this hypothesis has many problems to be solved.

In addition, the nerve cell-protective or neuroprotective action by a single use of ginsenoside $Rb_1$ has scarcely been elucidated until the studies on ginsenoside $Rb_1$ was initiated by us. We have studied until now to show a protective action of ginsenoside $Rb_1$ for the cells other than acetylcholine-containing nerve cells using the transient forebrain ischemia model of gerbils. It has been proved that in this forebrain ischemia model animal, occlusion of the bilateral common carotid arteries for 3 to 5 minutes while maintaining the brain temperature at 37° C. results in a neuronal loss of the hippocampal CA1 pyramidal cells (containing no acetylcholine) within one week after ischemia depending on the occlusion time (this event is called delayed neuronal death), and that the learning behavioral function of the ischemic animals is deteriorated (Wen T. -C. et al., Acta Neuropathol., 91, 15–22, 1996). These facts mean that the transient forebrain ischemia model of gerbils reflects the human pathologic condition of transient ischemic attack (TIA).

We have proved that administering ginsenoside $Rb_1$ (10 mg/kg or 20 mg/kg) into the peritoneal cavity of gerbil once a day for one week in advance can significantly prevent delayed neuronal death and learning disability caused by occlusion of the common carotid arteries for 5 minutes (Wen T. -C. et al., Acta Neuropathol., 91, 15–22, 1996). However, intraperitoneal administration of ginsenoside $Rb_1$ immediately after 3- or 5-minute occlusion of the common carotid arteries showed no effect (Wen T. -C. et al., Acta Neuropathol., 91, 15–22, 1996; Lim J. -H. et al., Neurosci. Res., 28, 191–200, 1997). Consequently, since transition rate and transportation rate to -brain of peripherally (intraperitoneally) administered ginsenoside $Rb_1$ are thought to be very low, no clinical application of ginsenoside $Rb_1$ was kept in mind at that stage in view of the protection of hippocampal CA1 pyramidal neurons.

It has been reported that intracerebroventricular infusion of ginsenoside $Rb_1$ starting immediately after occlusion of the common carotid arteries for 3 or 3.5 minutes in place of the above peripheral (intraperitoneal) administration suppresses the delayed neuronal death and learning disability (Lim J. -H. et al., Neurosci. Res., 28, 191–200, 1997). Further, in spontaneous hypertensive stroke-prone (SH-SP) rats with permanent occlusion of the cortical branch of the left middle cerebral artery (MCA) (cerebral infarction model of rats), intracerebroventricular infusion of ginsenoside $Rb_1$ starting immediately after permanent occlusion of the MCA caused a significant reduction of the infarcted area in the cerebral cortex and ameliorated the ischemia-induced place navigation disability of the animals (Zhang B. et al., J. Stroke Cerebrovasc. Dis., 7, 1–9, 1998).

Even though ginsenoside $Rb_1$ is effective in the direct intracerebroventricular infusion, however, it appears impossible to apply ginsenoside $Rb_1$ to human transient cerebral ischemic attack (TIA) and cerebral infarction due to the problems in the route of administration, similarly to other peptide growth factors (Sakanaka M. et al., Proc. Natl. Acad. Sci. USA, 95, 4635–4640, 1998; Wen T. -C. et al., J. Exp. Med., 188, 635–649, 1998).

Concerning the mechanism of neuroprotective action by peripheral (intraperitoneal) administration of ginsenoside $Rb_1$, we have reported that a culture medium previously admixed with a low concentration (1–100 fg/ml) of ginsenoside $Rb_1$ reduces neuronal necrosis caused by a hydroxyl radical inducer (ferrous sulfate) (Lim J. -H. et al., Neurosci. Res., 28, 191–200, 1997; Zhang B. et al., J. Stroke Cerebrovasc. Dis., 7, 1–9, 1998). We have presumed that ginsenoside $Rb_1$ decreases cell membrane lipid peroxides as a result of scavenging hydroxyl radicals to protect cultured nerve cells, but up to now no one proved this hypothesis.

Several reports concerning the neuroprotective effect of ginsenoside $Rb_1$ have been made in culture experiments. For example, high concentrations (0.11–11 µg/ml) of ginsenoside $Rb_1$ reduce glutamate-mediated neurotoxicity to prevent neuronal cell death (Kim Y. -C., et al., J. Neurosci. Res., 53, 426–432, 1998), and a higher concentration, approximately 500 µM (550 µg/ml) of ginsenoside $Rb_1$ has a possibility to prevent apoptosis-like nerve cell death (Tanaka T. et al., The Ginseng Review, 24, 61–65, 1998). However, according to the results of our culture experiments, high concentrations of ginsenoside $Rb_1$ has shown an increased neurotoxicity (Lim J. -H. et al., Neurosci. Res., 28, 191–200, 1997; Zhang B. et al., J. Stroke Cerebrovasc. Dis., 7, 1–9, 1998).

Furthermore, such high concentrations of ginsenoside $Rb_1$ can not be realized in an extracellular fluid in vivo, and we speculate that an administration of a large amount of ginsenoside $Rb_1$ into a human body to maintain the high extracelular concentrations of ginsenoside $Rb_1$ is impossible considering cost and adverse effects. Actually, from our experimental results, it has been proven that a high dose of ginsenoside $Rb_1$ can not always provide preferable efficacy and effectiveness (Zhang B. et al., J. Stroke Cerebrovasc. Dis., 7, 1–9, 1998).

In conclusion, the mechanism of neuroprotection by ginsenoside $Rb_1$ has not been elucidated yet. If the action mechanism of ginsenoside $Rb_1$ can be made clear, it is expected to find out new efficacies and applicabilities of the same agent. Further, it has not been elucidated whether or not ginsenoside $Rb_1$ actually inhibits apoptosis-like cell death at low concentrations.

We have found that ginsenoside $Rb_1$, at such a markedly low concentration range never reported in the world as 1 fg/ml to 100 fg/ml, suppresses apoptosis-like nerve cell death by increasing the expression of a cell death-suppressing gene product $Bcl\text{-}x_L$. Namely we have found in the present invention that ginsenoside $Rb_1$ is the only one non-peptidic $Bcl\text{-}x_L$ expression stimulator in the world. Although ginsenoside $Rb_1$ at the concentration of 100 fg/ml showed a slight suppressive action on the formation of lipid peroxides, no such effect was observed at a lower concentration range. Consequently, the hypothesis heretofore presented in relation to the action mechanism of ginsenoside $Rb_1$ was found inappropriate. We have further found that ginsenoside $Rb_1$ suppresses apoptosis-like nerve cell death in vivo, and completed the present invention.

Namely, we have found that intravenous administration of ginsenoside $Rb_1$ exhibits unexpectedly a superior suppressive action against cerebral infarction and ameliorates infarction-induced place navigation disability.

An object of the present invention is to provide drugs or pharmaceutics which exhibit a superior therapeutic effect on patients with cerebral infarction and a suppressive action for cerebrovascular dementia, and protect cells by facilitating an expression of the cell death-suppressing gene product $Bcl\text{-}x_L$.

Another object of the present invention is to provide preparations for efficaciously administering ginsenoside $Rb_1$ or its salt useful as cytoprotective agents.

More particularly, further object of the present invention is to provide pharmaceutical compositions comprising ginsenoside $Rb_1$ or its salt for inhibiting apoptosis or apoptosis-like cell death or pharmaceutical compositions comprising ginsenoside $Rb_1$ or its salt for promoting an expression of the cell death-inhibitory gene product $Bcl\text{-}x_L$.

Still further object of the present invention is to provide preparations comprising ginsenoside $Rb_1$ or its salt for intravenous administration useful for the therapy, prevention or treatment of brain and nerve diseases.

DISCLOSURE OF INVENTION

The present invention relates to pharmaceutical compositions comprising low concentrations of ginsenoside $Rb_1$ or its salt for inhibiting apoptosis or apoptosis-like cell death.

The present invention further relates to pharmaceutical compositions comprising low concentrations of ginsenoside $Rb_1$ or its salt for promoting expression of the cell death suppressing gene product $Bcl\text{-}x_L$.

The pharmaceutical composition of the present invention is preferably preparations for intravenous administration, but other routes of administration can optionally be selected.

The present invention still further relates to pharmaceutical compositions comprising ginsenoside $Rb_1$ or its salt preferably at low extracellular concentrations in lesion for the therapy, prevention or treatment of brain and nervous diseases, and more preferably the present invention relates to preparations comprising ginsenoside $Rb_1$ or its salt for intravenous administration for the therapy, prevention or treatment of the above diseases. Further, the present invention pertains to the hereinbefore described preparations for intravenous administration for the therapy, prevention or treatment of brain and nervous diseases, protective agents or preparations for brain cells or nerve cells, methods for treating or preventing these brain diseases, and to the use of ginsenoside $Rb_1$ or its salt for producing these pharmaceutical compositions.

BRIEF DESCRIPTION OF DRAWINGS

In FIG. 1, closed circles (●) indicate the results of rats with sham operation; and open circles (○) indicates the results of MCA-occluded rats infused with only physiological saline; closed squares (■) indicate the results of MCA-occluded rats infused with ginsenoside $Rb_1$ in a dose of 6 μg/day and open squares (□) indicate the results of MCA-occluded rats infused with ginsenoside $Rb_1$ in a dose of 60 μg/day.

BEST MODE FOR CARRYING OUT THE INVENTION

Figure 1B:
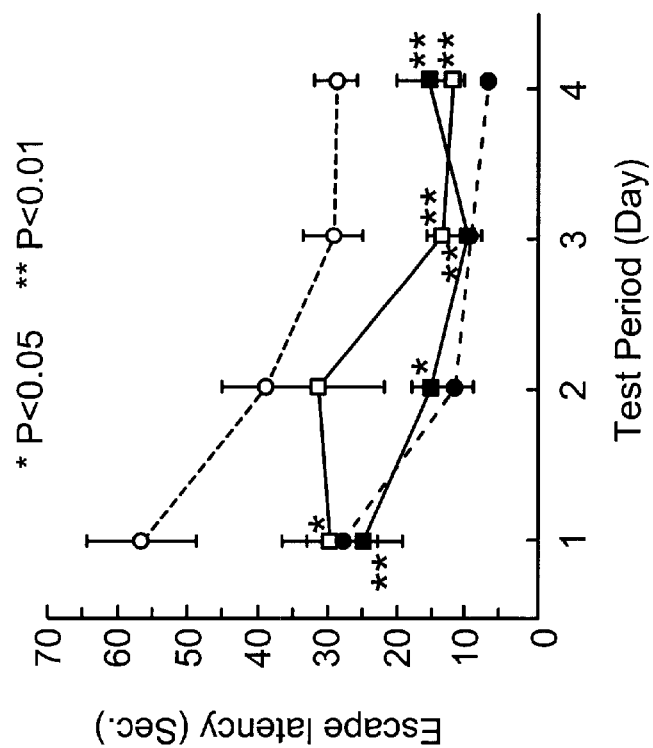
FIG. 1 shows the results of water maze tests. The left drawing in FIG. 1 shows the results of water maze tests at the second week after MCA occlusion and the right drawing shows the results of water maze tests at the fourth week after MCA occlusion.

Ginsenoside $Rb_1$ of the present invention is a compound represented by the formula hereinbefore. Ginsenoside $Rb_1$ can be isolated and purified according to the method of Shibata et al. (Shibata et al., Economic and medicinal plant research, World Scientific, Philadelphia, pp. 217–284, 1985). Ginsenoside $Rb_1$ purified by such a method has a purity more than 98%, which has been confirmed by thin layered chromatography and nuclear magnetic resonance spectrum (Kawashima Y. and Samukawa K., J. Med. Pharmacol. Soc. Wakan-Yaku, 3, 235–236, 1986). It is preferable to use highly purified ginsenoside $Rb_1$ of the present invention, but mixtures extracted from natural products or natural plants such as medicinal ginseng, which contains ginsenoside $Rb_1$ can also be used.

Ginsenoside $Rb_1$ of the present invention can be used in its free form, but can be used as its suitable salts. Its solvates such as hydrates can also be used.

The concentrations of ginsenoside $Rb_1$ used in the present invention are preferably low, more concretely, its concentration in extracellular fluid in lesion is 1 ng/ml or less, preferably 1 pg/ml or less, and more preferably 100 fg/ml or less. The preparations for intravenous administration of ginsenoside $Rb_1$ of the present invention should preferably be adjusted so that the concentrations of ginsenoside $Rb_1$ in extracellular fluid of the lesion tissue of patients are maintained in the concentration range hereinabove described. A sufficient favorable effect of the pharmaceutical compositions and preparations of the present invention can be obtained even at the concentrations of 1–100 fg/ml in the extracellular fluid of the lesion tissue. One of features of the present invention is to use ginsenoside $Rb_1$ preferably at the low extracellular concentrations in lesion.

Another feature of the present invention is to use ginsenoside $Rb_1$ as preparations for intravenous administration. Quite surprisingly, it was found that intravenously administered ginsenoside $Rb_1$, unlike peripherally (intraperitoneally) administered ginsenoside $Rb_1$, was transferred rapidly to the central nervous system. The preparations for intravenous administration of the present invention may be those, which can be directly administered intravascularly, preferably intravenously, and may optionally be those for single intravenous infusion or for continuous intravenous infusion. It can also be a formulation used to be added to preparations for intravenous administration such as a composition for drip infusion.

Intravenous administration of ginsenoside $Rb_1$ of the present invention can reduce the infracted area to about ¼ in comparison with that of a non-administered control group, as well as having an unique mechanism of action that is to enhance the expression of a cell death-suppressing factor Bcl-$x_L$. It also protects nerve cells or neurons in the brain. Consequently, it can be applied as neuroprotective agents for not only acute and chronic cerebral infarction but also acute or chronic cerebral hemorrhage, subarachnoidal hemorrhage and cerebral embolism or transient cerebral ischemic attack (TIA).

Namely, ginsenoside $Rb_1$ of the present invention is the drug or pharmaceutical composition, which can be administered intravenously as a drip infusion in an ambulance car to a patient suspected to suffer from cerebral apoplexy. The pathologic condition of cerebral ischemia has been known to be generated not only by cerebral infarction but also by cardiac failure, severe anemia, respiration disorders, cardiac arrest and ventricular fibrillation. In order to protect the brain against these diseases and to improve prognosis of patients with the diseases, the pharmaceutical composition comprising ginsenoside $Rb_1$ of the present invention is quite effective.

The pharmaceutical composition comprising ginsenoside $Rb_1$ of the present invention is expected to exhibit an efficacy through an enhanced expression of Bcl-$x_L$ protein on the other primary and secondary neurodegenerative diseases accompanied by apoptosis-like neuron death (Alzheimer's disease, Pick's disease, spinocerebellar degeneration, Parkinson's disease, chorea, glaucoma, senile macular degeneration, amyotrophic lateral sclerosis, AIDS encephalopathy, hepatic encephalopathy, encephalitis, cerebral palsy, retinal pigment degeneration, head (brain) injury, spinal cord injury, carbon monoxide poisoning, retinal detachment, neonatal asphyxia, diabetic retinopathy, peripheral nerve diseases, etc.).

Further, a specific feature of the medicinal preparations comprising ginsenoside $Rb_1$ of the present invention, which should not be overlooked, is the fact that it does not show any adverse effects. For example, even though ginsenoside $Rb_1$ is added to normal cultured nerve cells or neurons, which are not treated with sodium nitroprusside (SNP), a nitric oxide (NO) donor, it shows no effect on neuronal metabolic activity. Moreover, ginsenoside $Rb_1$ at low extracellular concentrations (1–100 fg/ml) protects only nerve cells injured by treating with SNP, (refer to example 3). Consequently, ginsenoside $Rb_1$ does not affect normal neuronal functions but can give a favorable effect only on the lesion tissue. This point can be emphasized as a more superior property of ginsenoside $Rb_1$ than glutamate receptor antagonists under developing as neuroprotective agents at present.

It has also been reported that no effects of intracerebroventricular administration of ginsenoside $Rb_1$ on brain temperature, cerebral blood flow and blood pressure are observed (Lim J. -H. et al. Neurosci. Res., 28, 191–200, 1998). No adverse effect was detected within a range of careful observation on animals, to which ginsenoside $Rb_1$ of the present invention was administered.

Ginsenoside Rb1 pf of the present invention, when administered to rats with permanent MCA occlusion (body weight about 300 g) in a dose of 6 μg/day or 60 μg/day, resulted in a reduction of the cerebral infarction area and ameliorated ischemia-induced place navigation disability (cerebrovascular dementia). Based on these experimental results, a dose range for human patients with cerebral apoplexy (body weight 60 kg) is calculated as 1.2 mg -12 mg/day. However, since required dose amount per body weight is, generally, decreased depending on the increased body weight of animals, a dose of 1.2 mg or less is thought to exhibit a sufficient effect. Daily doses of the pharmaceutical composition of the present invention is, though depending on an individual difference and a disease state of the patient, 0.1 mg or more, preferably 1 mg or more, more preferably 10 mg or more. Dosages less than 0.1 mg/day are also contemplated if the extracellular concentration of ginsensoside $Rb_1$ or its salt in lesion tissue is kept at 1 ng/ml or less. The lowest dosage ginsenoside $Rb_1$ or its salt for systematic daily administration is approximately 10 fg, based on the effective concentration range of ginsenoside $Rb_1$ or its salts in vitro. Since the pharmaceutical composition of the present invention has less adverse effect, it can be administered considerably in large amount as an upper limit of dosage, and the upper limit of dosage is 1 g or less/day, preferably 0.1 g or less/day.

The method for administration of the pharmaceutical composition of the present invention is preferably intravenous administration and the amount of administration hereinabove described can be administered consecutively or repetitively. Ginsenoside $Rb_1$, an active ingredient of the present invention is a sort of saponin, and can be formulated by the conventional methods. For example, an aqueous pharmaceutical composition of the present invention can be prepared as a preparation for intravenous administration by dissolving lyophilized crystals in physiological saline, distilled water, phosphate buffer or glucose solution. Lipid microsphere or liposome preparation can also be used. The concentrations of ginsenoside $Rb_1$ or its salt in the preparations for intravenous administration can optionally be adjusted unless so high, for example 0.01–10 mg/ml, preferably 0.1–1 mg/ml.

In the animal experiments of the present invention, ginsenoside $Rb_1$ was intravenously administered continuously for 28 days after permanent occlusion of the cortical branch of the left middle cerebral artery (MCA). Since in the actual case of cerebral apoplexy at an acute phase, the brain lesion frequently becomes worse within 2 weeks after the onset, a sufficient effect can be expected if an administration of ginsenoside $Rb_1$ is performed during at least this period. As the results of practical use of ginsenoside $Rb_1$, applications to cerebrovascular reconstruction and reperfusion surgeries may be expanded.

The present invention takes initiative in disclosing suppression of apoptosis or apoptosis-like cell death as a result of promoting the expression of Bcl-$x_L$ protein by ginsenoside $Rb_1$ at low extracellular concentrations in lesion, which has never known in the past. The fact that ginsenoside $Rb_1$ at low extracellular concentrations in lesion suppresses apoptosis or apoptosis-like cell death by upregulating the expression of Bcl-$x_L$ protein, indicates that ginsenoside $Rb_1$ is effective for not only central nervous system (CNS) diseases but also peripheral tissue diseases accompanied with apoptosis (for example, rejection after organ transplantation, ischemia-reperfusion injury of heart, liver and kidneys, myocardial infarction, peripheral artery occlusion, peripheral circulatory failure, bedsore, autoimmune diseases and immunodeficiency). Moreover, for the treatment of these peripheral tissue diseases, smaller amounts of ginsenoside $Rb_1$ than those used for brain diseases can provide sufficient effect and efficacy.

Next, the actions of ginsenoside $Rb_1$ of the present invention at low concentrations are explained in detail.

First, we examined the actions of intravenous infusion of ginsenoside $Rb_1$. For this purpose, for example, male SH-SP rats weighing 250~300 g at the age of 12–13 weeks were used. The animals were bred in an air-conditioned room with a 12:12 hour light-dark cycle, and water and feeds were supplied ad libitum. The cortical branch of the left middle cerebral artery (MCA) was coagulated and cut. A single intravenous administration of ginsenoside $Rb_1$ dissolved in physiological saline was conducted immediately after MCA permanent occlusion (6 μg or 60 μg), thereafter continuous intravenous administration of ginsenoside $Rb_1$ was performed for 28 days by using an Alza mini osmotic pump (6 μg/day or 60 μg/day).

Control animals with MCA permanent occlusion (ischemic control animals) and sham-operated animals were administered with the same amount of physiological saline.

After MCA permanent occlusion, according to the conventional method (Zhang B. et al., J. Stroke Cerebrovasc. Dis., 7, 1–9, 1998), water maze tests were performed for 4 days at the 2nd week and the 4th week, respectively, and the place navigation abilities of SH-SP rats were determined.

Figure 1A:
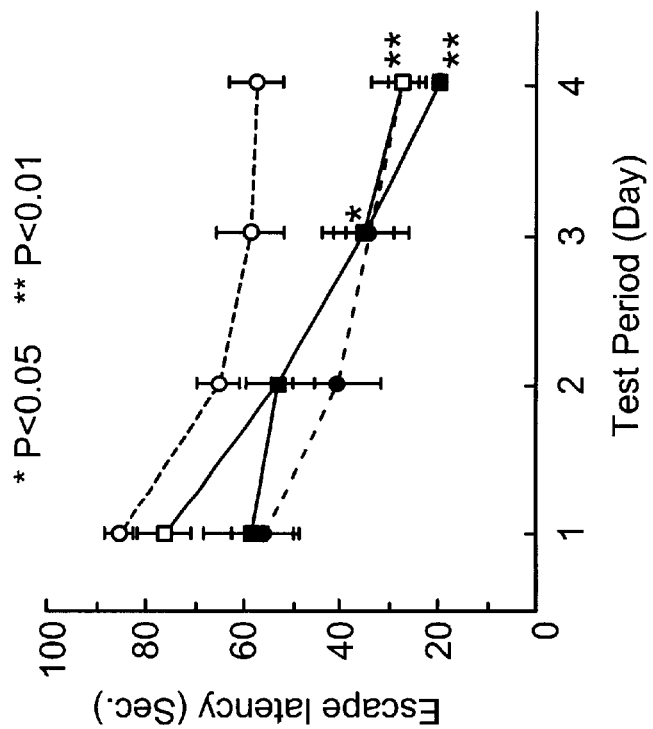

Results are shown in FIG. 1. The left drawing in FIG. 1 is the results of the 2nd week and the right drawing is the results of the 4th week after parmanent MCA occlusion. In FIG. 1, closed circles (●) indicate the results of rats with sham operation; and open circles (○) indicate the results of MCA-occluded rats administered with only physiological saline; closed squares (■) indicate the results of MCA-occluded rats administered with ginsenoside $Rb_1$ in a dose of 6 μg/day and open squares (□) indicate the results of MCA-occluded rats administered with ginsenoside $Rb_1$ in a dose of 60 μg/day.

As shown in FIG. 1, the place navigation disability after MCA permanent occlusion (after cerebral infarction) was significantly improved by ginsenoside $Rb_1$ infusion as compared with a group of cerebral infarction administered with physiological saline. Especially, in the water maze tests at the 2nd week and at the 4th week after MCA occlusion, the low dose of ginsenoside $Rb_1$ significantly ameliorated the learning disability on the 3rd day and on the 4th day, and the high dose of ginsenoside $Rb_1$ on the 4th day at the 2nd week and on the 3rd and 4th days at the 4th week after MCA occlusion. Significant effects were also noted on the 1st day at the 4th week in the high dose and the low dose groups, respectively. No significant differences in swimming speed of SH-SP rats were observed among the four experimental groups.

After the water maze tests at the 4th week, the SH-SP rats were anesthetized with chloral hydrate, and they were perfused and fixed transcardially with 0.1 mole phosphate buffer containing 4% paraformaldehyde. The brains were dissected out and cerebrocortical infarcted areas were photographed. Areas of the left cerebral hemisphere and the left cerebrocortical infarct lesions were measured on the photographs by using an image analysis device. The left cerebrocortical infarcted areas were divided by the left cerebral hemispheric areas to calculate ratios of the cerebrocortical infarction (%). Results are shown in FIG. 2.

Figure 2:
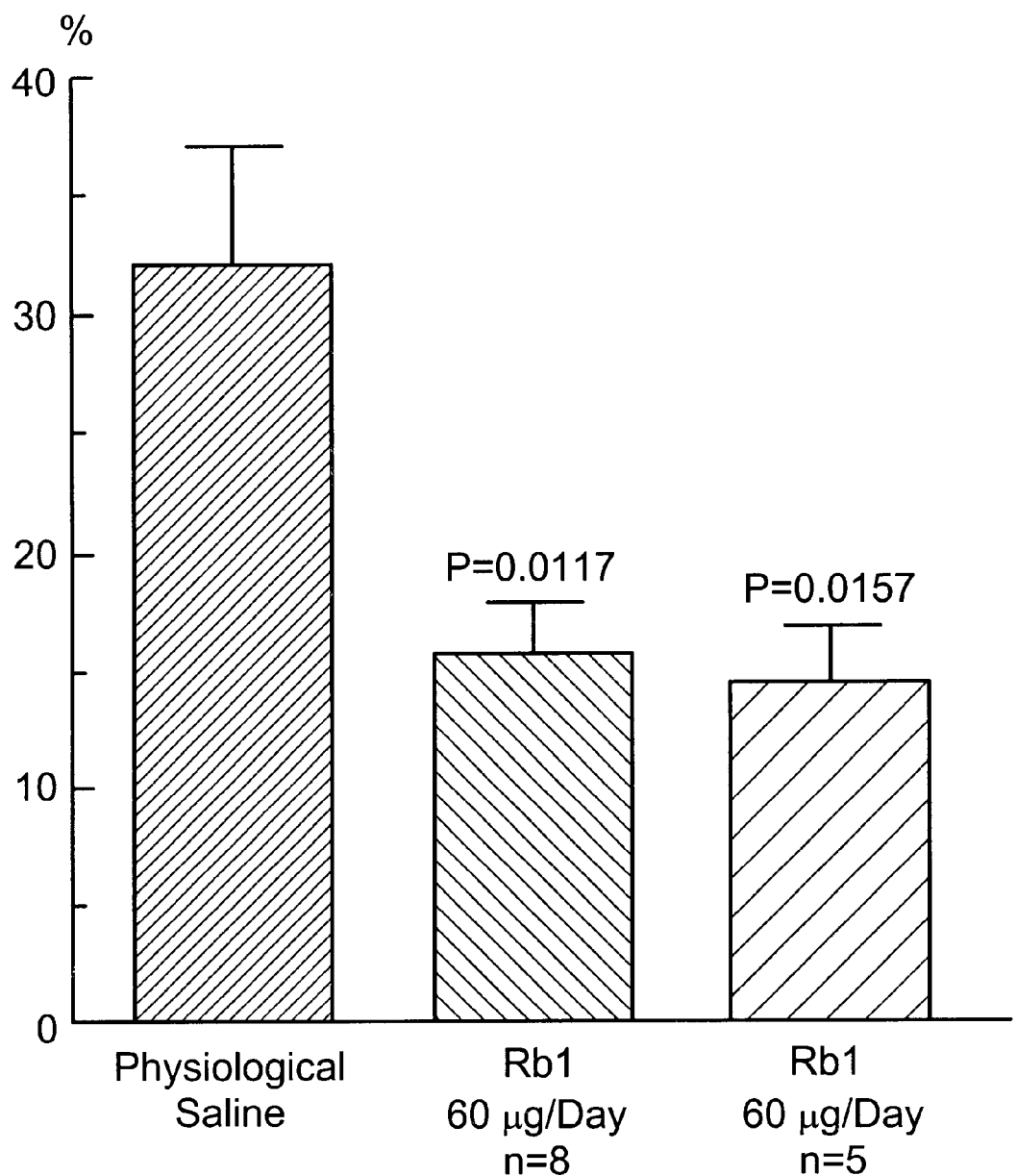
FIG. 2 is a figure showing ratios of cerebrocortical infarction.

As shown in FIG. 2, the ratio of cerebrocortical infarction was significantly reduced in the groups of cerebral infarction with intravenous administration of ginsenoside $Rb_1$ as compared with the group of cerebral infarction with administration of physiological saline. Since the ratio of cerebrocortical infarction is calculated based on the area of infarction, and the mean value of the ratios in the groups intravenously administered with ginsenoside $Rb_1$ is reduced to 50% or less compared with that of the group administered with physiological saline, actual volume of infarction appears to be reduced to about ¼ by intravenous administration of ginsenoside $Rb_1$.

Figures 3A, 3B:
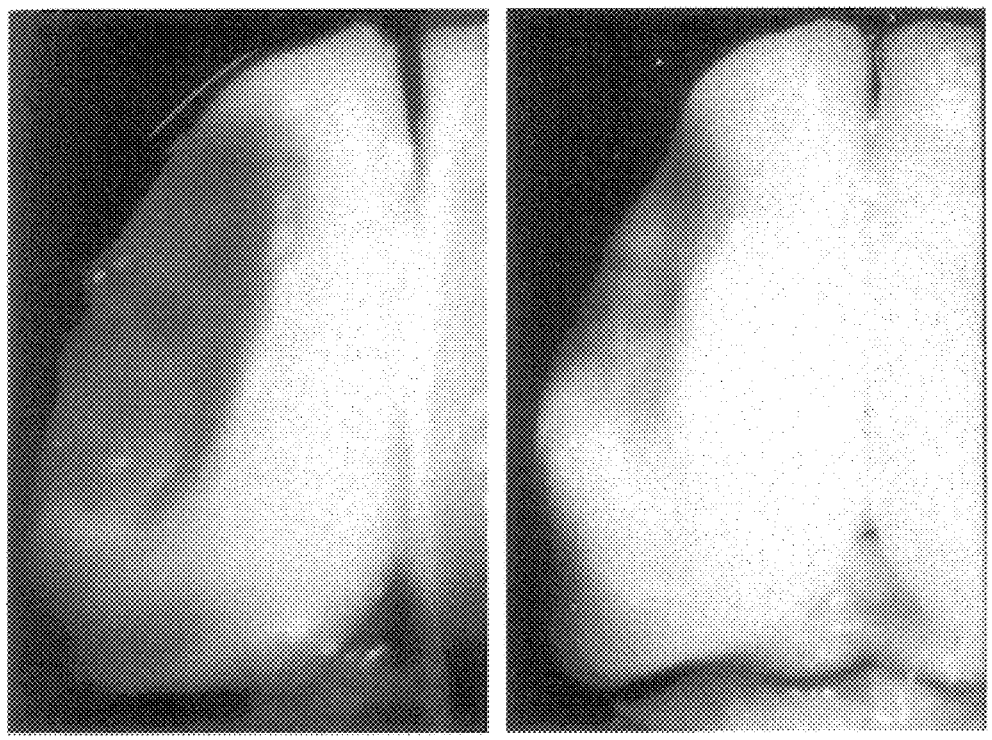
FIG. 3 is a photograph showing infarcted lesion in the cerebral cortex. A: MCA-occluded rat infused with physiological saline and B: MCA-occluded rat infused with ginsenoside $Rb_1$ in a dose of 6 μg/day.

An actual case of cerebral infarct area of the group administered with physiological saline and an actual case of cerebral infarct area of the group administered with ginsenoside $Rb_1$ (6 μg/day) are shown in FIG. 3A and FIG. 3B, respectively.

Figure 4:
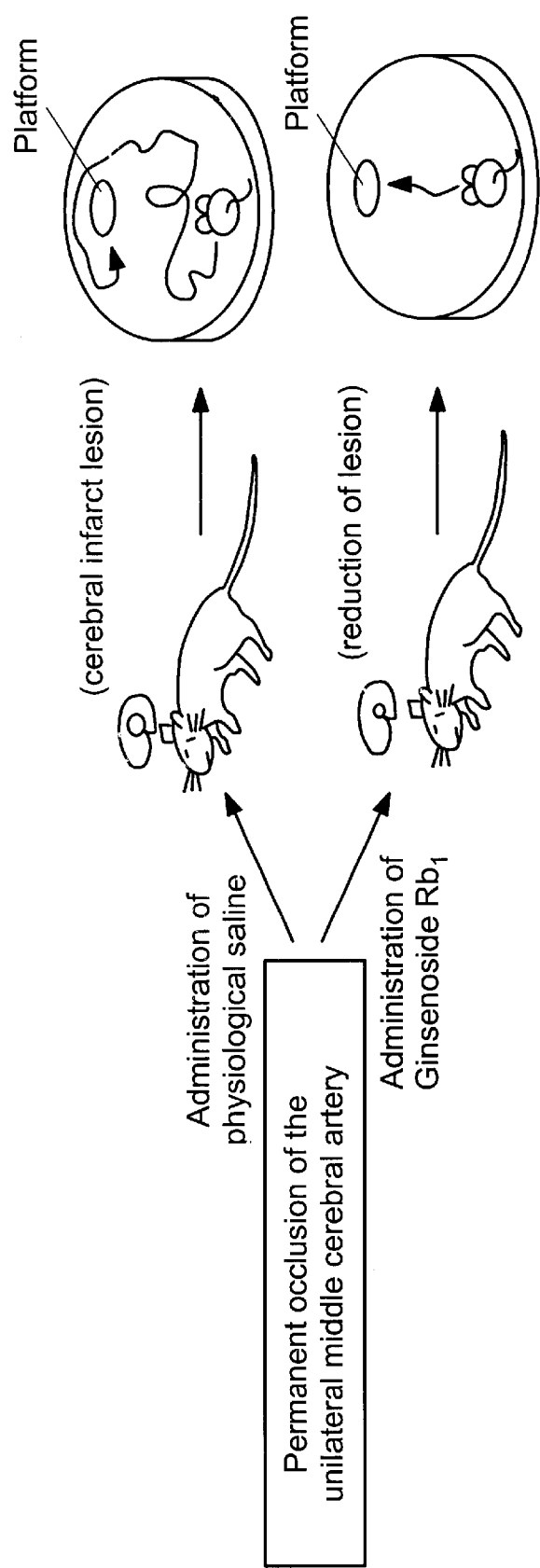
FIG. 4 is a schematic drawing summarizing the results of example 1 hereinbelow described.

FIG. 4 is a schematic drawing summarizing the results of the present experiments. In rats administered with physiological saline, the size of cerebral infarction ramained large and it took a long time for the rats to escape onto the goal platform in the water maze tests. Contrary, in rats administered with ginsenoside $Rb_1$ of the present invention, the infarct area was recovered and reduced, and as a result, in the water maze tests, only a short time was required for the rats to arrive at the goal platform.

According to the paper of the present inventors in the past using a transient forebrain ischemia model of gerbils (Wen T. -C., et al., Acta Neuropathol., 91, 15–22, 1996), even if intraperitoneal administration of ginsenoside $Rb_1$ (10 mg/kg/day or 20 mg/kg/day) was performed before ischemic loading, only about 30% of hippocampal CA1 pyramidal neurons could be rescued. In addition, intraperitoneal administration of ginsenoside $Rb_1$ in gerbils after the ischemic event resulted in no effect. Moreover, since the daily doses of intraperitoneally administered ginsenoside $Rb_1$ are as high as 0.7 mg–1.4 mg determined by the body weight of gerbils (approximately 70 g), considering from the view point of efficacy and effect of ginsenoside $Rb_1$ administration, intravenous administration of ginsenoside $Rb_1$ is a superior method for administration than the intraperitoneal administration, and can be easily applied to humans. As well known, an intraperitoneal administration to human cannot always be applied except for a partial exception (peritoneal lavage, etc.).

Animals with MCA permanent occlusion (cerebral infarction rats) used in the present example are obviously more severe than the transient forebrain ischemia model of gerbils and they provide a model close to human disease that is cerebral infarction. Consequently, the fact that the intraveous infusion of gisenoside $Rb_1$ starting after cerebrovascular occlusion exhibited a marked favorable effect on rats with permanent MCA occlusion clearly indicates the usefulness, convenience and economical advantage of intravenous infusion of ginsenoside $Rb_1$ in low doses.

On the other hand, in the previous report, in which ginsenoside $Rb_1$ was directly infused into the cerebral ventricles of animals with MCA permanent occlusion (Zhang B., et al., J. Stroke Cerebrovasc. Dis., 7, 1–9, 1998), a significant suppressive effect on cerebral infarction was observed only when the continuous intracerebroventricular infusion of ginsenoside $Rb_1$ at the dose of 0.6 μg/day was conducted after MCA occlusion; and the effect was equal to or a little less than the effect of intravenous administration of ginsenoside $Rb_1$ as shown in the present example. In the previous report on the intracerebroventricular administration of ginsenoside $Rb_1$, no curative effect on cerebral infarction was observed even when the other doses of ginsenoside $Rb_1$ (6 μg/day or 0.06 μg/day) were continuously infused into the cerebral ventricles after MCA permanent occlusion. Consequently, the effective dose range of intracerebroventricularly administered ginsenoside $Rb_1$ was very narrow and its practical use for clinical medicine was thought to be difficult. Moreover, the actual application of intracerebroventricularly infused ginsenoside $Rb_1$ to humans appears to be impossible when we consider the balance between its risk and benefit.

Generally, a neuroprotective factor or agent exhibits the maximum effect when directly administered into the cerebral ventricles or into the brain parenchyma, and in case of intravenous or intraperitoneal administration, its effect and efficacy seem to drastically decrease or disappear due to the blood brain barrier that prevents the neuroprotective agent from entering the brain parenchyma. Consequently, based on the experimental results of intraperitoneal administration or intracerebroventricular administration of ginsenoside $Rb_1$, the effect and efficacy of intravenously infused ginsenoside could not be anticipated at all.

As clarified by the present invention, however, intravenous administration of ginsenoside $Rb_1$ reduces effectively the cerebral infarct area of rats with MCA permanent occlusion in a wider dose range than in case of intracerebroventricular administration, and improves learning ability of the MCA-occluded animals. Ginsenoside $Rb_1$ is a purified saponin, which is contained in medicinal ginseng, but since it can not be detected in blood after oral administration, a pharmacological action of ginsenoside $Rb_1$ per se has been substantially denied. However, according to the present example, it is clarified that intravenous administration of ginsenoside $Rb_1$ has effect, efficacy and use independent of the medicinal ginseng.

Next, we conducted experiments to determine the preventive effect of ginsenoside $Rb_1$ on peroxidation of nerve cell membrane lipids.

According to the method of Peng et al. (Peng H. et al., J. Cereb. Blood Flow Metab., 18, 349–360, 1998), cerebrocortical neurons from rats at embryonic age 17 were maintained in a serum-free culture medium for 3 days, and thereafter the medium was replaced with a fresh culture medium containing or not containing ginsenoside $Rb_1$ and the neurons were incubated for further 48 hours. Then the medium was changed to a fresh medium containing ferrous sulfate and ascorbic acid but not containing ginsenoside $Rb_1$ and the neuronal culture was maintained for 2 hours to generate hydroxyl radicals for giving an oxidative injury to neuronal membrane. The generated neuronal membrane lipid peroxide was determined by photometrically measuring a fixed amount of thiobarbituric acid (TBA) after solubilizing the cells with sodium dodecyl sulfate.

An object of the present experiment is to examine whether ginsenoside $Rb_1$ can prevent peroxidation of cell membrane lipid within the concentration range (0.1–100 fg/ml) required for suppressing nerve cell necrosis caused by ferrous sulfate, or not.

Figure 5:
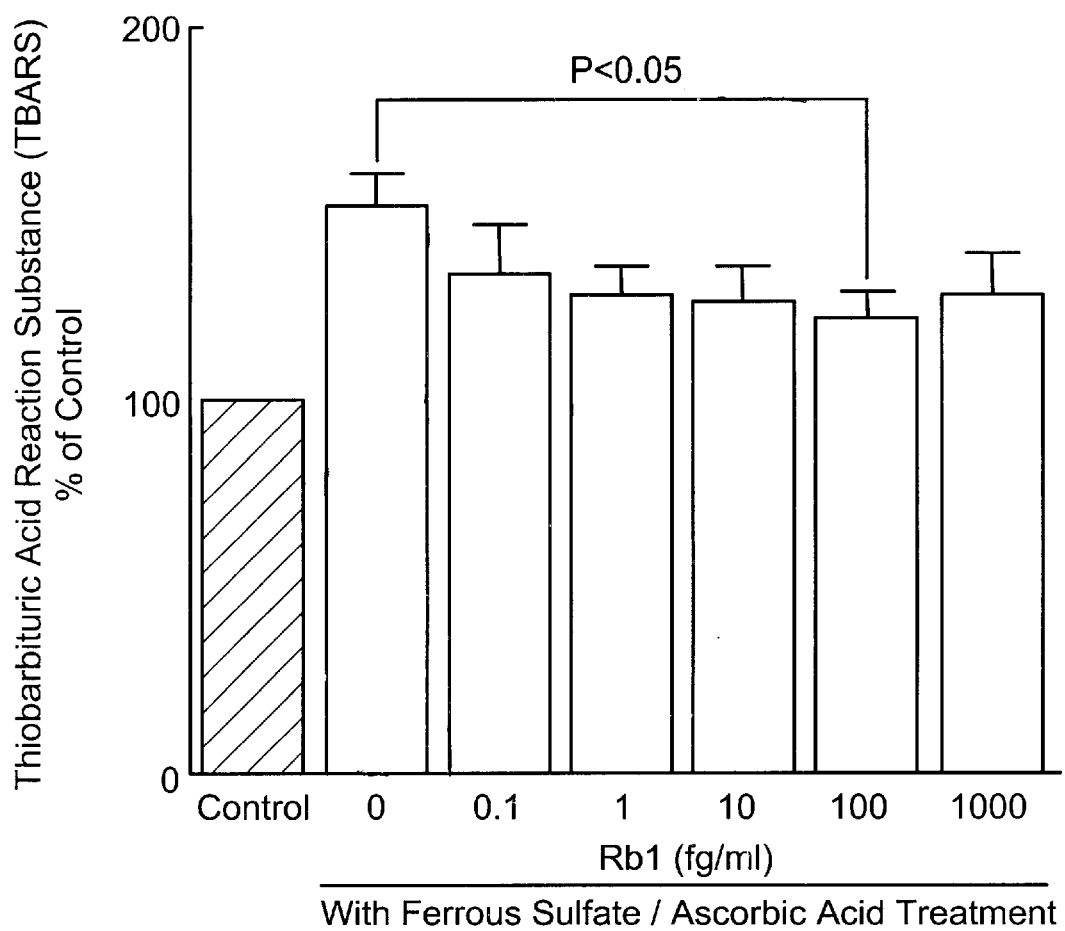
FIG. 5 is a drawing, which shows a very weak preventive effect of ginsenoside $Rb_1$ on peroxidation of membrane lipids.

Results are shown in FIG. 5. From the experimental results, a preventive effect of ginsenoside $Rb_1$ on the peroxidation of nerve cell membrane lipid could be slightly confirmed only at the concentration of 100 fg/ml, and no preventive effects on lipid peroxidation were observed in the concentration range of 0.1–10 fg/ml, in which free radical damage caused by ferrous sulfate was reduced. Consequently, as reported in the previous papers (Lim J. -H., et al., Neurosci. Res., 28, 191–200, 1997; Zhang B., et al., J. Stroke Cerebrovasc. Dis., 7, 1–9, 1998), ginsenoside $Rb_1$ in the concentration range of 0.1–100 fg/ml, could surely reduce the neurotoxicity of free radicals. However, the prior hypothesis that subsequently ginsenoside $Rb_1$ also suppresses lipid peroxide formation was found to be obviously incorrect. Consequently, the present experiment demonstrates a necessity for the analysis of a new mechanism underlying the action of ginsenoside $Rb_1$.

For that purpose, we performed experiments to determine a suppressive action of ginsenoside $Rb_1$ on nerve cell death (apoptosis).

Cell death is classified roughly into necrosis and apoptosis depending on their morphological features. Concerning the nerve cell death, a concept for necrosis has been established. As for a concept for neuronal apoptosis, however, typical features such as those observed in lymphocytes are very rarely noted, although a similar phenomenon is observed in the matured brain under pathologic conditions. Consequently, in the present specification, gradually progressing nerve cell death, which is different from necrosis, is defined as "apoptosis of nerve cells" or "apoptosis-like nerve cell death".

We recently found that as a result of a short time exposure of cultured nerve cells (or neurons) to a nitric oxide (NO) donor, sodium nitroprusside (SNP), apoptosis of nerve cells was induced (Toku K., et al., J. Neurosci. Res., 53, 415–425, 1998). Since a typical feature of apoptosis was observed in this culture experiment, a suppressive effect of ginsenoside $Rb_1$ on apoptosis was judged with the use of this experimental system.

After maintaining cerebrocortical nerve cells (neurons) from rats at embryonic age 17 in a serum-free culture medium for 4 or 5 days, the medium was replaced with a fresh medium containing or not containing ginsenoside $Rb_1$ and the neurons were incubated for 24 hours. Then, SNP at the concentration of 100 $\mu$M was added to the medium for 10 minutes, and the nerve cells (neurons) were maintained in a medium containing ginsenoside $Rb_1$ for 16 hours. Survival rate of the nerve cells was measured by using a redox indicator, alamar blue.

In the previous ferrous sulfate-loading experiments, ginsenoside $Rb_1$ was added in advance to the culture medium and results were determined. In the present experiments, ginsenoside $Rb_1$ was added before and after SNP loading or only after SNP loading, and its effects were measured.

Figure 6:
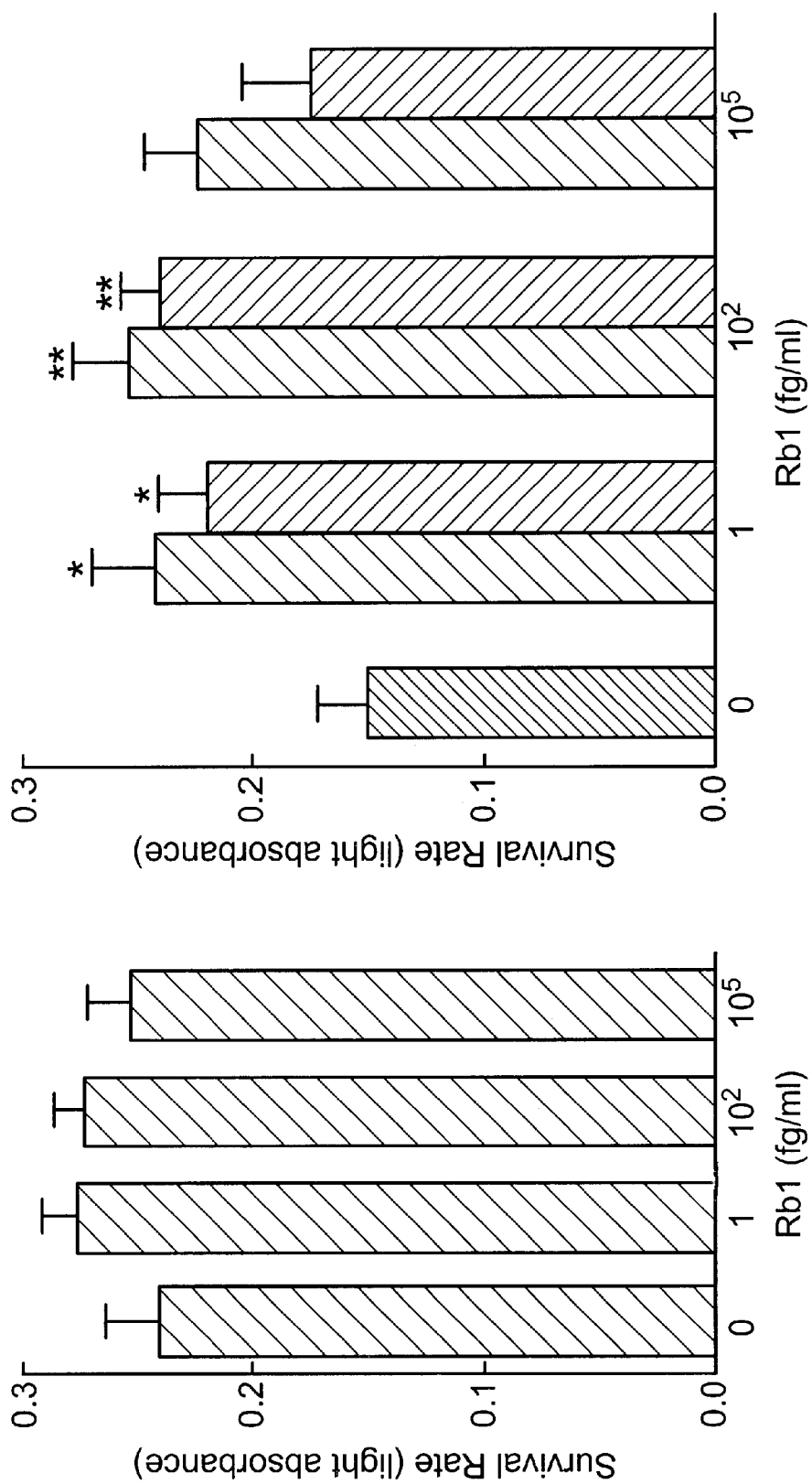
FIG. 6 is a graph showing an inhibitory action of ginsenoside $Rb_1$ on nerve cell death (apoptosis) caused by sodium nitroprusside (SNP). In the left drawing of FIG. 6, results without SNP treatment, and in the right drawing, results with SNP treatment are shown, respectively. Black out columns show addition of ginsenoside $Rb_1$ before and after SNP treatment, and columns with slant lines show addition of ginsenoside $Rb_1$ after treatment with SNP.

Results are shown in FIG. 6. In the right drawing of FIG. 6, results with SNP treatment are shown. Black out columns show additions of ginsenoside $Rb_1$ before and after SNP treatment, and columns with slant lines show an addition of ginsenoside $Rb_1$ after treatment with SNP.

As shown in the left drawing of FIG. 6, in the case of no treatment with the nitric oxide (NO) donor, sodium nitroprusside (SNP), no significant effects of ginsenoside $Rb_1$ on the metabolic activity of cultured nerve cells were observed. As a result of SNP treatment, nerve cell death (apoptosis) occurred without addition of ginsenoside $Rb_1$ (the first column from the left in the right drawing of FIG. 6), but ginsenoside $Rb_1$ in the concentrations of 1–100 fg/ml significantly suppressed apoptosis of nerve cells, even in the cases of its administrations before and after SNP treatment or only after SNP treatment.

Results of the present experiments, in which ginsenoside $Rb_1$ proved to suppress apoptosis of nerve cells even at the low concentrations such as 1–100 fg/ml in the extracellular fluid, very low concentrations ever known before, actually demonstrated the possibility of applying ginsenoside $Rb_1$ to the treatment or therapy of pathologic apoptosis-like nerve cell death for the first time in the world.

Next, experiments for analyzing an action of ginsenoside $Rb_1$ on $Bcl-x_L$ expression were performed.

$Bcl-x_L$ gene is expressed in many tissues such as tissues of mature brain, immune systems and circulatory systems, and is proved to play important roles in the survival of cells (Adams J. M. and Cory S., Science, 281, 1322–1326, 1998; Boise, L. H., et al., Cell, 74, 597–608, 1993; Gottschalk A. R., et al., Proc. Natl. Acad. Sci. USA, 91, 7350–7354, 1994; Gonzalez-Garcia M., et al., Proc. Natl. Acad. Sci. USA, 92, 4304–4308, 1995).

It was investigated whether ginsenoside $Rb_1$ of the present invention can increase the expression of $Bcl-x_L$ gene or not. Experimental techniques followed those by Wen et al. (Wen T. -C., et al., J. Exp. Med., 188, 635–649, 1998). Total RNA was extracted from cultured nerve cells treated for 24 hours with ginsenoside $Rb_1$ at the concentrations of 0 fg/ml, 1 fg/ml and 100 fg/ml. cDNA was prepared from DNase-treated total RNA (3 $\mu$g) by using oligo dT primer and reverse transcriptase (Moloney murine leukemia virus reverse transcriptase). Gene amplification reaction (polymerase chain reaction, PCR) was performed by using Taq polymerase under the following conditions: (1) 94° C., 2 minutes; (2) 94° C., 1.5 minute; 55° C., 1.5 minute; 72° C., 2 minutes constructed one cycle, and 25 cycles for $Bcl-x_L$ and 20 cycles for $\beta$-actin were performed; and (3) 72° C., 2 minutes.

PCR products were electrophoresed on 3% agarose gel and visualized by ethidium bromide staining. The expression of $\beta$-actin mRNA was used as an internal standard. Results are shown in FIG. 7.

Figure 8:
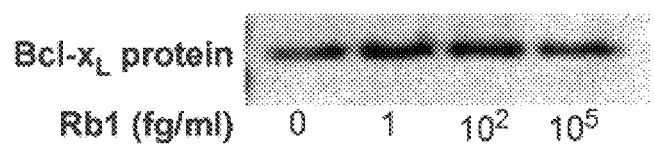
FIG. 8 is a photograph instead of drawing, showing the result of Western blotting for Bcl-$x_L$ protein in neurons treated with ginsenoside $Rb_1$.

In order to investigate whether ginsenoside $Rb_1$ enhanced the expression of $Bcl-x_L$ protein in nerve cells or not, Western blotting using anti-Bcl-$x_L$ protein antibody was performed. After culturing rat cerebrocortical neurons for 48 hours with or without ginsenoside $Rb_1$, the neurons (nerve cells) were solubilized in a sample buffer for electrophoresis and electrophoresed. Electrophorates were transferred to nitrocellulose membrane to perform Western blotting. Results are shown in FIG. 8.

Figure 9:
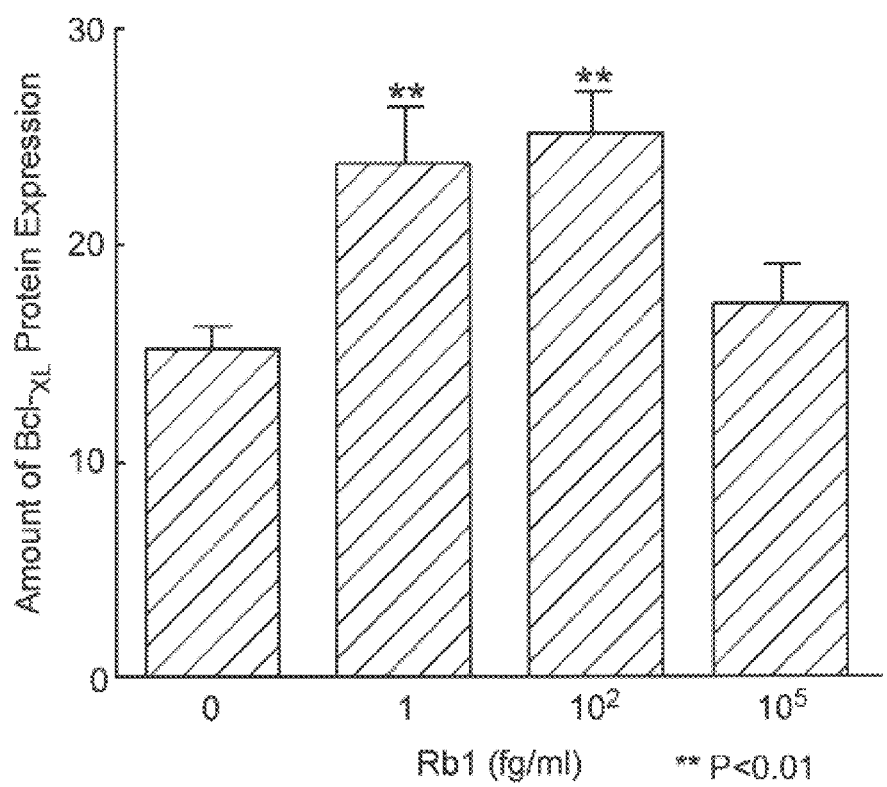
FIG. 9 is a graph quantifying the results of Western blotting for Bcl-$x_L$ protein in neurons treated with ginsenoside $Rb_1$.

Further, bands reacted with the anti-Bcl-$x_L$ protein antibody were quantified by using an image analyzer. Results are shown in FIG. 9.

Figure 7:
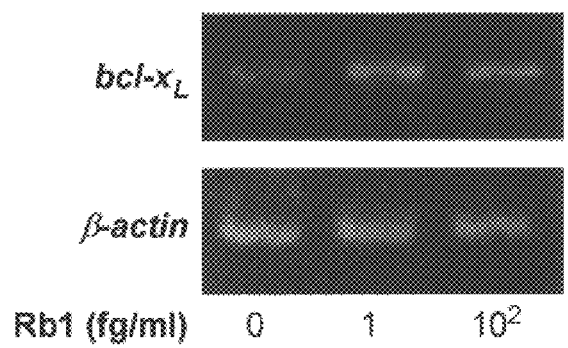
FIG. 7 is photographs instead of drawings, showing upregulation of Bcl-$x_L$ mRNA expression by ginsenoside $Rb_1$.

As shown in FIG. 7, in the cultured nerve cells treated with ginsenoside $Rb_1$ at the concentration of 1 fg/ml or 100 fg/ml, the expression of Bcl-$x_L$ mRNA was increased as compared with the control (0 fg/ml). Ginsenoside $Rb_1$ in the concentration range of 1–100 fg/ml exhibiting a suppressive effect on apoptosis-like nerve cell death, significantly increased the amount of neuronal Bcl-$x_L$ protein expression by approximately 50% (FIG. 8 and FIG. 9).

Among bioactive substances facilitating the expression of Bcl-$x_L$ protein in nerve cells or neurons, interleukin 3 in the concentration range of 0.6–15.0 ng/ml has been reported (Wen T. -C., et al., J. Exp. Med., 188, 635–649, 1998). The upregulation by ginsenoside $Rb_1$ of Bcl-$x_L$ protein expression was exhibited at far lower concentrations than that by interleukin 3, and was more potent than interleukin 3 which could increase slightly the expression of Bcl-$x_L$ protein by about 10%. Interleukin 3 could exhibit a neuroprotective action only by direct intracerebroventricular administration, but ginsenoside $Rb_1$ was proved to protect cerebral nerve cells or cerebral neurons by intravenous administration in the experiment hereinbefore described (example 1). Consequently, ginsenoside $Rb_1$ is the only one expression enhancer of Bcl-$x_L$ protein expression in the world at present among non-peptide neurotropic substances, which can be peripherally administered. Heretofore, nobody could expect that the non-peptide medicine showed a more potent activity for facilitating Bcl-$x_L$ protein expression than the peptide factor (interleukin 3). Peptide factor, which can enhance even slightly the expression of Bcl-$x_L$ protein in nerve cells, was only interleukin 3, as far as we know.

It is said that the mitochondrion-associated protein Bcl-$x_L$ inhibits binding of Apaf1 to procaspase 9 as a result of its binding with Apaf1 (Adams J. M. and Cory S., Science, 281, 1322–1326, 1998). If a decrease or a functional decline of Bcl-$x_L$ protein occurs, Apaf1 is released from Bcl-$x_L$ protein to activate procaspase 9, concomitant with a leakage of cytochrome C from mitochondria (Adams J. M. and Cory S., Science, 281, 1322–1326, 1998). Once cytoplasmic procaspase 9 is activated, subsequently caspase 9 and caspase 3 are activated, and a process, in which cells are autolyzed by the actions of these proteases to enter apoptosis, is accelerated. At the stage activating procaspase 9, the cell appears to be committed to death, and therefore prevention or inhibition of the activation of procaspase 9 by an enhancer of Bcl-$x_L$ protein expression (ginsenoside $Rb_1$) is a wise method to preclude cell death.

In order to analyze a suppressive effect of ginsenoside $Rb_1$ on intracerebral apoptosis-like neuron death, the present inventors examined whether actually occurring pathological apoptosis-like neuron death in the mature brain can be reduced by administration of ginsenoside $Rb_1$ or not. The three minute forebrain ischemia model of gerbils was used as model animal. It was reported that at one week after 3 minute ischemia, about one half of hippocampal CA1 pyramidal neurons degenerated (Sakanaka M., et al., Proc. Natl. Acad. Sci. USA, 95, 4635–4640, 1998). However, the present inventors demonstrated that fragmentation of nerve cell nuclei, an index of apoptosis-like cell death, in the remaining nerve cells was further in progress at this moment, using TUNEL staining (Wen T. -C., et al., J. Exp. Med., 188, 635–649, 1998; Peng H., et al., J. Cereb. Blood Flow Metab., 18, 349–360, 1998). With this model animal, it was examined with TUNEL staining whether apoptosis-like neuron death on the 7th day after 3 minute ischemia could be suppressed by intracerebroventricular administration of ginsenoside $Rb_1$ or not.

Immediately after 3 minute forebrain ischemia in gerbils under inhalation anesthesia, a single intracerebroventricular administration of ginsenoside $Rb_1$ at the dose of 2.5 ng or 25 ng was performed, and subsequently ginsenoside $Rb_1$ (60 ng/day or 600 ng/day) was continuously infused into the cerebral ventricles through an osmotic minipump for 1 week. At one week after 3 minute forebrain ischemia, the gerbils were perfused and fixed transcardially with phosphate buffer containing 4% paraformaldehyde under pentobarbital anesthesia and the brain was dissected out. The brain was embedded in paraffin, and paraffin sections 5 μm thick were cut. TUNEL staining was performed in accordance with the conventional method. Control animals were infused with an equal amount of physiological saline.

Results are shown in FIG. 10. FIG. 10(A) shows a control animal; (B) shows an animal administered with ginsenoside $Rb_1$ in a dose of 60 ng/day; and (C) shows an animal administered with ginsenoside $Rb_1$ in a dose of 600 ng/day.

Figure 10A:
FIGS. 10(A), (B) and (C) are photomicrographs instead of drawings, showing the inhibition by ginsenoside $Rb_1$ of pathologic apoptosis-like neuron death in the matured brain.
Figure 10B:
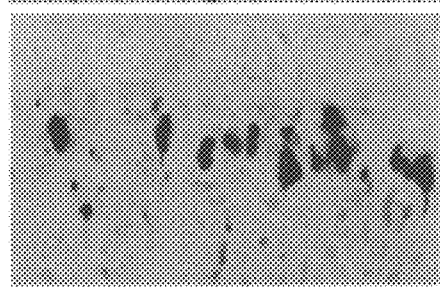
FIG. 10(D) is a graph quantifying their results.
Figure 10C:
Figure 10D:
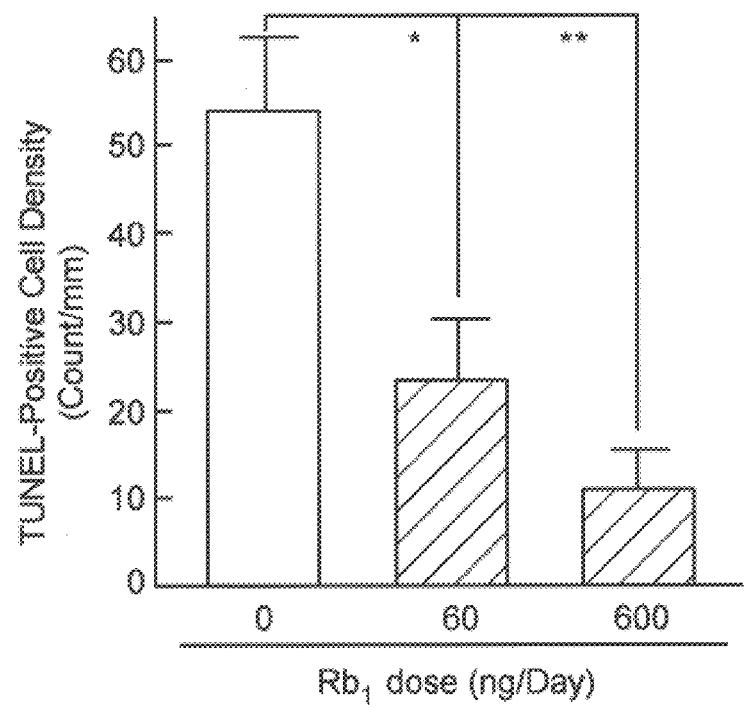

As shown in FIG. 10(A), in the hippocampal CA1 field of gerbils loaded with 3 minute forebrain ischemia, a large number of TUNEL-positive neurons appeared at 1 week after ischemia. This suggests that the neurons are on the way of apoptosis-like cell death. As a result of the intracerebroventricular administration of ginsenoside $Rb_1$ immediately after 3 minute forebrain ischemia, TUNEL-positive nerve cells were significantly reduced in a dose-dependent manner [FIG. 10(B), 10(C), 10(D)]. This indicates that the results of the culture experiments in examples 3 and 4 can be applied in vivo. It has already been reported that ginsenoside $Rb_1$ could not affect cerebral blood flow or brain temperature (Lim J. -H., et al., Neurosci. Res., 28, 191–200, 1997; Zhang B., et al., J. Stroke Cerebrovasc. Dis., 7, 1–9, 1998).

The above experimental results have demonstrated that preparations comprising ginsenoside $Rb_1$ or its salt for intravenous administration were effective at very low concentrations for therapy, prevention or treatment of brain and nervous diseases such as cerebrovascular dementia, cerebral infarction, cerebral apoplexy and transient cerebral ischemic attack (TIA).

It has also been demonstrated that ginsenoside $Rb_1$ or its salt suppresses apoptosis or apoptosis-like cell death at low extracellular concentrations of 1 ng/ml or less, in more detail 1 pg/ml or less, in further more detail 1–100 fg/ml. Further, it has also been found that ginsenoside $Rb_1$ or its salt promotes expression of the cell death-suppressing gene product Bcl-$x_L$.

Ginsenoside $Rb_1$ or its salt is known as a component of medicinal ginseng and is very low in toxicity.

The present invention provides clinically useful therapeutic or preventive agents for brain and nervous diseases. The therapeutic or preventive agents for brain and nervous diseases of the present invention are preferably in preparations for intravenous administration. To be more specific, the preparations for intravenous administration of the present invention and the brain cell- or nerve cell-protective agents comprising ginsenoside $Rb_1$ or its salt should be adjusted so that the extracellular concentrations of ginsenoside $Rb_1$ or its salt in lesion tissues are kept at 1 ng/ml or less, preferably at 1 pg/ml or less, and more preferably at 1–100 fg/ml.

EXAMPLES

The present invention will be explained in detail by concrete examples, but the present invention is not limited within these examples.

Example 1

Experiment on Intravenous Infusion of Ginsenoside $Rb_1$

Male SH-SP rats at the age of 12–13 weeks, weighing 250–300 g, were used. The animals were bred in a room furnished with 12 hours light and dark cycles and water and feeds were supplied ad libitum. Blood pressure of the animals was 203±6.9 mmHg. The following experiments were conducted in accordance with the Guide for Animal Experimentation at Ehime University School of Medicine. The cortical branch of the left middle cerebral artery (MCA) of SH-SP rats, were coagulated and cut, while their rectal temperature was maintained at 37±0.2° C. under inhalation anesthesia.

Immediately after MCA permanent occlusion, 60 $\mu$l of physiological saline containing ginsenoside $Rb_1$ at a concentration of 1 $\mu$g/$\mu$l or 0.1 $\mu$g/$\mu$l was injected once into the left femoral vein. Then a catheter connected to an Alza osmotic minipump implanted subcutaneously in the back of each animal was inserted into the same vein from the point of the single injection of ginsenoside $Rb_1$. Physiological saline containing ginsenoside $Rb_1$ was filled in advance in the said osmotic minipump, and ginsenoside $Rb_1$ in a dose of 60 $\mu$g/day or 6 $\mu$g/day was continuously infused into the blood stream through the catheter placed in the left femoral vein for 28 days. Flow rate of the ginsenoside $Rb_1$-containing solution was 0.25 $\mu$l/hour.

Control animals with MCA permanent occlusion (ischemic control animals) and sham-operated animals received the same amount of physiological saline.

After the MCA permanent occlusion according to the conventional method (Zhang B. et al., J. Stroke Cerebrovase. Dis., 7, 1–9, 1998), water maze tests were performed for 4 days at the 2nd week and the 4th week, respectively, and place navigation abilities of SH-SP rats were determined.

Results are shown in FIG. 1. The left drawing of FIG. 1 is the results of the 2nd week and the right drawing is the results of the 4th week after permanent MCA occlusion. In FIG. 1, closed circles (●) indicate the results of rats with sham operation; and open circles (○) indicate the results of MCA-occluded rats administered with only physiological saline; closed squares (■) indicate the results of MCA-occluded rats administered with ginsenoside $Rb_1$ in a dose of 6 $\mu$g /day and open squares (□) indicate the results of MCA-occluded rats administered with ginsenoside $Rb_1$ in a dose of 60 $\mu$g/day. Data are represented as a mean±SE. Statistical analyses were conducted by ANOVA+Fisher's PLSD.

No significant differences in swimming speed were observed among the four experimental groups.

After termination of the water maze tests at the 4th week, the SH-SP rats were anesthetized with chloral hydrate, and they were perfused and fixed transcardially with 0.1 mole phosphate buffer containing 4% paraformaldehyde. The brains were dissected out and cerebrocortical infarcted areas were photographed. Areas of the left cerebral hemisphere and the left cerebrocortical infarct lesions were measured on the photographs by using an image analysis device. The left cerebrocortical infarcted areas were divided by the left cerebral hemispheric areas to calculate ratios of the cerebrocortical infarction (%). Results are shown in FIG. 2.

An actual case of a cerebral infarct lesion of the group administered with physiological saline and an actual case of a cerebral infarct lesion of the ginsenoside $Rb_1$ (6 $\mu$g/day)-administered group are shown in FIG. 3A and FIG. 3B, respectively.

FIG. 4 is a schematic drawing summarizing the results of the present experiments. In rats administered with physiological saline, the size of cerebral infarction remained large, and in the water maze tests, it took a long time for the rats to escape onto the goal platform. Contrary, in rats administered with ginsenoside $Rb_1$ of the present invention, the infarct area was recovered and reduced, and as a result, in the water maze tests, only a short time was required for the rats to arrive at the goal platform.

Example 2

Experiments on a Preventive Effect of Ginsenoside $Rb_1$ on Peroxidation of Neuronal Membrane Lipids Cerebrocortical neurons from rats at embryonic age 17, were maintained in a serum-free culture medium for 3 days, and thereafter the medium was replaced with a fresh culture medium containing ginsenoside $Rb_1$ at the concentrations of 0.1 fg/ml, 1 fg/ml, 10 fg/ml, 100 fg/ml and 1000 fg/ml or not containing ginsenoside $Rb_1$ (0 fg/ml) and the neurons were incubated for further 48 hours. Then the medium was changed to a fresh medium containing ferrous sulfate and ascorbic acid but no ginsenoside $Rb_1$, and the neuronal culture was maintained for 2 hours to generate hydroxyl radicals for giving oxidative injury to neuronal membrane. The generated neuronal membrane lipid peroxide was photometrically determined by measuring the fixed amount of thiobarbituric acid (TBA) after solubilizing the cells with sodium dodecyl sulfate.

Results are shown in FIG. 5. From the experimental results, a preventive effect of ginsenoside $Rb_1$ on peroxidation of nerve cell membrane lipid could be slightly confirmed only at the concentration of 100 fg/ml, and no preventive effects on lipid peroxidation were observed in the concentration range of 0.1–10 fg/ml, in which free radical damage caused by ferrous sulfate was reduced.

Example 3

Experiments for Judging a Suppressive Action of Ginsenoside $Rb_1$ on Nerve Cell Death (Apoptosis)

After maintaining cerebrocortical nerve cells (neurons) from rats at embryonic age 17 in a serum-free culture medium for 4 or 5 days, the medium was replaced with a fresh medium containing ginsenoside $Rb_1$ at the concentrations of 1 fg/ml, 100 fg/ml and 100 pg/ml or no ginsenoside $Rb_1$ (0 fg/ml), and the neurons were incubated for 24 hours. Thereafter a nitric oxide (NO) donor, sodium nitroprusside (SNP) at a concentration of 100 $\mu$M, was added to the medium for 10 minutes. Then the nerve cells (neurons) were maintained in a medium containing ginsenoside $Rb_1$ for 16 hours. Survival rate of the nerve cells was measured by using a redox indicator, alamar blue.

Results are shown in FIG. 6. In the left drawing of FIG. 6, results without SNP treatment are shown; ginsenoside $Rb_1$ did not affect the (metabolic) activity of neurons without SNP treatment. In the right drawing of FIG. 6, results with SNP treatment are shown. Black out columns show an addition of ginsenoside $Rb_1$ before and after SNP treatment, and columns with slant lines show an addition of ginsenoside $Rb_1$ after treatment with SNP. Data are represented as a mean±SE. Statistical analyses were conducted by ANOVA+Fisher's PLSD. Asterisks indicate significant differences against the cases without addition of ginsenoside $Rb_1$ ($*p<0.05$, $**p<0.01$).

As shown in the left drawing of FIG. 6, in the case of no treatment with the nitric oxide (NO) donor, sodium nitroprusside (SNP), no significant effects of ginsenoside $Rb_1$ on the metabolic activity of cultured nerve cells were observed. As a result of SNP treatment, nerve cell death (apoptosis) occurred without addition of ginsenoside $Rb_1$ (the first column from the left in the right drawing of FIG. 6), but ginsenoside $Rb_1$ in the concentration range of 1–100 fg/ml significantly suppressed apoptosis of nerve cells, and even in the cases of its administrations before and after SNP treatment or only after SNP treatment.

Example 4

Experiments for Analyzing an Action of Ginsenoside $Rb_1$ on Bcl-$x_L$ Expression In order to investigate whether ginsenoside $Rb_1$ of the present invention can increase the expression of Bcl-$x_L$ gene or not, total RNA was extracted from cultured nerve cells treated for 24 hours with ginsenoside $Rb_1$ at the concentrations of 0 fg/ml, 1 fg/ml and 100 fg/ml, in accordance with the experimental techniques of Wen et al. (Wen T. -C., et al., J. Exp. Med., 188, 635–649, 1998). cDNA was prepared from DNase-treated total RNA (3 $\mu$g) by using oligo dT primer and reverse transcriptase (Moloney murine leukemia virus reverse transcriptase). cDNA was amplified by PCR. The PCR was performed with the use of Taq polymerase under the following conditions: (1) 94° C., 2 minutes; (2) 94° C., 1.5 minute; 55° C., 1.5 minute; 72° C., 2 minutes constructed one cycle, and 25 cycles for Bcl-$x_L$ and 20 cycles for β-actin were performed; and (3) 72° C., 2 minutes.

PCR products were electrophoresed on 3% agarose gel and visualized by an ethidium bromide staining. The expression of β-actin mRNA was used as an internal standard. Results are shown in FIG. 7.

In addition, in order to investigate whether or not ginsenoside $Rb_1$ enhanced the expression of Bcl-$x_L$ protein in nerve cells, Western blotting using anti-Bcl-$x_L$ protein antibody was performed. After culturing rat cerebrocortical neurons for 48 hours with or without ginsenoside $Rb_1$, the neurons (nerve cells) were solubilized in a sample buffer for electrophoresis and electrophoresed. The electrophorates were transferred to nitrocellulose membrane to perform Western blotting. Results are shown in FIG. 8.

Further, bands reacted with the anti-Bcl-$x_L$ protein antibody were quantified by using an image analyzer. Results are shown in FIG. 9. Statistical analyses were conducted by ANOVA+Fisher's PLSD. Asterisks in the figure indicates significant differences ($**p<0.01$) against the cases without addition of ginsenoside $Rb_1$.

As shown in FIG. 7, in the cultured nerve cells treated with ginsenoside $Rb_1$ at the concentration of 1 fg/ml or 100 fg/ml, the expression of Bcl-$x_L$ mRNA was increased as compared with the control (0 fg/ml). Ginsenoside $Rb_1$ in the concentration range of 1–100 fg/ml exhibiting a suppressive effect on apoptosis-like nerve cell death, significantly increased the amount of Bcl-$x_L$ protein expression in apoptosis-like nerve cells by about 50% (refer to FIG. 9).

Example 5

Analysis of a Suppressive Effect of Ginsenoside $Rb_1$ on Intracerebral Apoptosis-Like Neuron Death Immediately after 3 minute forebrain ischemia in gerbils under inhalation anesthesia, a single intracerebroventricular administration of ginsenoside $Rb_1$ at the dose of 2.5 ng or 25 ng was performed, and subsequently ginsenoside $Rb_1$ (60 ng/day or 600 ng/day) was continuously infused into the cerebral ventricles for 1 week through an osmotic minipump. At one week after 3 minute forebrain ischemia, the gerbils were perfused and fixed transcardially with phosphate buffer containing 4% paraformaldehyde under pentobarbital anesthesia and the brain was dissected out. The brain was embedded in paraffin, and paraffin sections 5 $\mu$m thick were cut. TUNEL staining was performed in accordance with the conventional method. Control animals were infused with an equal amount of physiological saline.

Results are shown in FIG. 10. Statistical analyses in FIG. 10(D) were conducted by Mann-Whitney's U-test. FIG. 10(A) shows a control animal; (B) shows an animal administered with ginsenoside $Rb_1$ in a dose of 60 ng/day; and (C) shows an animal administered with ginsenoside $Rb_1$ in a dose of 600 ng/day.

As shown in FIG. 10(A), in the hippocampal CA1 field of gerbils loaded with 3 minute forebrain ischemia, a large number of TUNEL-positive neurons appeared at 1 week after ischemia. This suggests that the neurons are on the way of apoptosis-like cell death. As a result of the intracerebroventricular administration of ginsenoside $Rb_1$ immediately after 3 minute forebrain ischemia, TUNEL-positive nerve cells were significantly reduced in a dose-dependent manner [FIGS. 10(B), 10(C), 10(D)]. This indicates that the results of the culture experiments in examples 3 and 4 can be applied in vivo. It has already been reported that ginsenoside $Rb_1$ can not affect cerebral blood flow or brain temperature (Lim J. -H., et al., Neurosci. Res., 28, 191–200, 1997; Zhang B., et al., J. Stroke Cerebrovasc. Dis., 7, 1–9, 1998).

Industrial Applicability

The present invention provides extremely effective preparations comprising ginsenoside $Rb_1$ at low extracellular concentrations in lesion for the therapy, treatment or prevention of brain and nervous diseases such as cerebral infarction, cerebral hemorrhage, subarachnoidal hemorrhage, cerebral embolism or transient cerebral ischemic attack at acute or chronic phase, and provides neuroprotective agents or preparations for intravenous administration comprising ginsenoside $Rb_1$ at low extracellular concentrations in lesion. Namely, the present invention relevant to ginsenoside $Rb_1$ provides drugs that can be intravenously administered by drip infusion to a patient suspected to have cerebral apoplexy even in an ambulance car. Since in a case of acute cerebral apoplexy the lesion frequently becomes worse within 2 weeks after the onset of brain attack, if ginsenoside $Rb_1$ of the present invention can be administered at least within this period (for example for one day or 14 days), a sufficient effect can be expected. Further, as a result of practical use of ginsenoside $Rb_1$ in clinical medicine, surgical applications to cerebral angioplasty and/or reperfusion in patients with cerebral apoplexy would be expanded.

The pharmaceutical composition comprising ginsenoside $Rb_1$ or its salt of the present invention enhances the expression of Bcl-$x_L$ protein and thus appears to be effective for other primary and secondary neurodegenerative diseases accompanied with apoptosis-like nerve cell death (Alzheimer's disease, Pick's disease, spinocerebellar degeneration, Parkinson's disease, chorea, glaucoma, amyotrophic lateral sclerosis, senile macular degeneration, AIDS encephalopathy, hepatic encephalopathy, diabetic retinopathy, encephalitis, cerebral palsy, retinal detachment, head or brain injury, spinal cord injury, demyelinating diseases, neonatal asphyxia, peripheral nerve diseases, retinal pigment degeneration, etc.).

The pharmaceutical composition of the present invention provides a drug with high safety since it has little adverse effect.

The present invention discloses that ginsenoside $Rb_1$ suppresses apoptosis or apoptosis-like cell death by promoting the expression of Bcl-$x_L$ protein at low extracellular concentrations in lesion, which has never been known in the past. This fact indicates that ginsenoside $Rb_1$ is effective for not only central nervous system (CNS) diseases but also peripheral tissue diseases accompanied with apoptosis or apoptosis-like cell death (for example, rejection after organ transplantation, cardiac insufficiency or heart failure, cardiomyopathy, ischemia-reperfusion injury of heart, liver and kidneys, glossodynia, myocardial infarction, radiation injury, peripheral artery occlusion, peripheral circulatory failure, bedsore, corneal injury, autoimmune diseases and immunodeficiency) or protection of organs and tissues for transplantation. For the therapy or treatment of these peripheral tissue diseases, smaller amounts of ginsenoside $Rb_1$ than those used for CNS diseases can exhibit sufficient effect and efficacy. In addition, the pharmaceutical composition comprising ginsenoside $Rb_1$ or its salt of the present invention can be used as preparations not only for intravenous administration but also for nasal drops, inhalation, sublingual tablets, suppositories, preparation for topical application, external preparations for skin, preparations for oral administration, eye drops, spreading for local application, intramuscular injection, subcutaneous injection and intracutaneous injection. Further, the pharmaceutical composition of the present invention can be used as preparations for oral administration by mixing, encapsulating or binding ginsenoside $Rb_1$ with carriers which can inhibit decomposition in the digestive tract or stimulate absorption in the digestive tract.

What is claimed is:

1. A pharmaceutical composition consisting essentially of ginsenoside Rb1 or its salt and carriers for intravenous administration, wherein doses or dosages of ginsenoside $Rb_1$ or its salt are adjusted to between 1.67 mg/kg/day and 0.167 fg/kg/day.

2. A preparation adapted for single intravenous administration comprising a pharmaceutical composition of claim 1.

3. A preparation adapted for continuous intravenous administration comprising a pharmaceutical composition of claim 1.

4. A method for therapy, prevention or treatment of brain and nervous diseases comprising administering to a subject in need of treatment ginsenoside $Rb_1$ or its salt in a dose range of 1.67 mg/kg/day to 0.167 fg/kg/day.

5. The method according to claim 4, wherein the subject is suffering from or susceptible to a brain-related disease or disorder.

6. The method of claim 4, wherein the subject is suffering from or susceptible to a nervous disease or disorder.

7. The method according to claim 4, wherein the brain and nervous diseases are cerebrovascular dementia, cerebral infraction, cerebral apoplexy or transient cerebral ischemic attack.

8. The method according to claim 4, wherein the administration is intravenous administration.

9. A method for promoting the cell death-inhibitory gene product Bcl-$x_L$, comprising administering to a subject in need of treatment ginsenoside Rb1 or its salt in a dose range of 1.67 mg/kg/day to 0.167 fg/kg/day.

10. A method for inhibiting apoptosis or apoptosis-like cell death, comprising administering to a subject in need of treatment ginsenoside Rb1 or its salt in a dose range of 1.67 mg/kg/day to 0.167 fg/kg/day.

11. A method for manufacturing preparations for therapy, prevention or treatment of brain and nervous diseases comprising formulating a preparation comprising ginsenoside $Rb_1$ or its salt.

12. The method according to claim 11, wherein the preparations for therapy, prevention or treatment are preparations for intravenous administration.

* * * * *